(12) United States Patent
Ginn et al.

(10) Patent No.: US 11,234,845 B2
(45) Date of Patent: Feb. 1, 2022

(54) EXPANDABLE INTRODUCER SHEATH

(71) Applicant: Medtronic, Inc., Minneapolis, MN (US)

(72) Inventors: Richard S. Ginn, Gilroy, CA (US); Michael T. Carley, San Jose, CA (US)

(73) Assignee: Medtronic, Inc., Minneapolis, MN (US)

( * ) Notice: Subject to any disclaimer, the term of this patent is extended or adjusted under 35 U.S.C. 154(b) by 724 days.

(21) Appl. No.: 14/276,952

(22) Filed: May 13, 2014

(65) Prior Publication Data

US 2015/0094795 A1 Apr. 2, 2015

Related U.S. Application Data

(60) Provisional application No. 61/824,471, filed on May 17, 2013.

(51) Int. Cl.
*A61F 2/962* (2013.01)
*A61L 29/08* (2006.01)
(Continued)

(52) U.S. Cl.
CPC ............ *A61F 2/962* (2013.01); *A61L 29/041* (2013.01); *A61L 29/06* (2013.01); *A61L 29/085* (2013.01);
(Continued)

(58) Field of Classification Search
CPC .......................... A61M 25/0662–0668; A61M 2025/0675–0687; A61M 25/0021–0023;
(Continued)

(56) References Cited

U.S. PATENT DOCUMENTS

| 4,655,771 A | 4/1987 | Wallsten |
| 4,723,549 A | 2/1988 | Wholey et al. |
(Continued)

FOREIGN PATENT DOCUMENTS

| AU | 2012335016 A1 | 5/2014 |
| AU | 2012335016 B2 | 7/2017 |
(Continued)

OTHER PUBLICATIONS

"International Search Report and Written Opinion" dated Oct. 17, 2014, International Patent Application No. PCT/US14/37924 with International Filing Date of May 13, 2014, (8 pages).
(Continued)

*Primary Examiner* — Brooke Nicole Labranche
(74) *Attorney, Agent, or Firm* — Innovation Counsel LLP

(57) ABSTRACT

One embodiment is directed to a system for deploying a device to a distal location across a vessel, comprising an elongate introducer sheath tubing member comprising open-cell fibrous wall material defining a lumen therethrough, wherein in a collapsed configuration the sheath has a first cross-sectional outer diameter and a first lumen inner diameter, and in an expanded configuration, the sheath has a second cross-sectional outer diameter and a second lumen inner diameter; and a substantially non-porous expandable layer coupled to a proximal portion of sheath and configured to prevent fluids present in the lumen from crossing the fibrous wall material.

7 Claims, 15 Drawing Sheets

(51) Int. Cl.
*A61L 29/06* (2006.01)
*A61L 29/04* (2006.01)
*A61L 29/14* (2006.01)
*A61F 2/24* (2006.01)
*A61M 25/00* (2006.01)
*A61M 25/06* (2006.01)

(52) U.S. Cl.
CPC ........... *A61L 29/146* (2013.01); *A61F 2/2436* (2013.01); *A61F 2002/9623* (2020.05); *A61M 25/0662* (2013.01); *A61M 2025/0024* (2013.01)

(58) Field of Classification Search
CPC ... A61M 2025/0024–0025; A61M 2039/0626; A61M 29/00; A61F 2/2427–2439; A61F 2/95–97; A61F 2002/9505–9665; A61F 2/2436; A61F 2/962; A61B 17/3431–3439; A61B 17/3468; A61B 2017/3433; A61L 29/06; A61L 29/041; A61L 29/14; A61L 29/085; A61L 29/146
USPC ................................ 606/108; 600/184, 208
See application file for complete search history.

(56) References Cited

U.S. PATENT DOCUMENTS

| | | | |
|---|---|---|---|
| 4,954,126 A | 9/1990 | Wallsten | |
| 5,061,275 A | 10/1991 | Wallsten et al. | |
| 5,221,261 A | 6/1993 | Termin et al. | |
| 5,290,295 A * | 3/1994 | Querals | A61M 25/104 604/264 |
| 5,415,664 A | 5/1995 | Pinchuk | |
| 5,527,282 A | 6/1996 | Segal | |
| 5,863,366 A | 1/1999 | Snow | |
| 5,911,702 A | 6/1999 | Romley et al. | |
| 5,941,896 A | 8/1999 | Kerr | |
| 5,997,508 A | 12/1999 | Lunn et al. | |
| 6,090,072 A | 7/2000 | Kratoska et al. | |
| 6,179,851 B1 | 1/2001 | Barbut | |
| 6,692,462 B2 * | 2/2004 | Mackenzie | A61B 17/3415 604/104 |
| 6,706,033 B1 | 3/2004 | Martinez et al. | |
| 7,014,647 B2 | 3/2006 | Brady et al. | |
| 7,766,820 B2 | 8/2010 | Core | |
| 8,206,280 B2 | 6/2012 | Evans et al. | |
| 8,591,539 B2 | 11/2013 | Gellman | |
| 9,370,438 B2 | 6/2016 | Ginn | |
| 9,545,298 B2 | 1/2017 | Ginn et al. | |
| 9,555,214 B2 | 1/2017 | Ren et al. | |
| 10,179,048 B2 | 1/2019 | Marchand et al. | |
| 2001/0041919 A1 | 11/2001 | Tsugita et al. | |
| 2001/0053929 A1 | 12/2001 | Vonesh et al. | |
| 2002/0016564 A1 | 2/2002 | Courtney et al. | |
| 2002/0077596 A1 | 6/2002 | McKenzie et al. | |
| 2002/0077598 A1 | 6/2002 | Yap et al. | |
| 2003/0050658 A1 | 3/2003 | Trask et al. | |
| 2003/0144670 A1 | 7/2003 | Pavcnik et al. | |
| 2004/0153117 A1 | 8/2004 | Clubb et al. | |
| 2004/0215167 A1 | 10/2004 | Belson | |
| 2004/0260331 A1 | 12/2004 | D'aquanni et al. | |
| 2005/0021125 A1 | 1/2005 | Stack et al. | |
| 2005/0149113 A1 | 7/2005 | Douk et al. | |
| 2005/0216053 A1 | 9/2005 | Douk et al. | |
| 2006/0052750 A1 * | 3/2006 | Lenker | A61B 17/3439 604/164.01 |
| 2006/0271093 A1 | 11/2006 | Holman et al. | |
| 2006/0282154 A1 | 12/2006 | Oepen et al. | |
| 2007/0016280 A1 | 1/2007 | Yacoby et al. | |
| 2007/0244501 A1 | 10/2007 | Horn et al. | |
| 2008/0167705 A1 | 7/2008 | Agnew | |
| 2008/0188928 A1 | 8/2008 | Salahieh et al. | |
| 2008/0195137 A1 | 8/2008 | Alleyne et al. | |
| 2008/0243068 A1 | 10/2008 | Ramzipoor | |
| 2009/0005675 A1 | 1/2009 | Grunwald et al. | |
| 2009/0024202 A1 | 1/2009 | Dave et al. | |
| 2009/0137900 A1 | 5/2009 | Bonner et al. | |
| 2009/0182278 A1 | 7/2009 | Eversull | |
| 2009/0182360 A1 | 7/2009 | Makower | |
| 2009/0240202 A1 * | 9/2009 | Drasler | A61M 25/0023 604/164.03 |
| 2009/0254169 A1 | 10/2009 | Spenser et al. | |
| 2009/0287182 A1 | 11/2009 | Bishop et al. | |
| 2010/0094392 A1 | 4/2010 | Nguyen et al. | |
| 2010/0100167 A1 | 4/2010 | Bortlein et al. | |
| 2010/0174355 A1 | 7/2010 | Boyle et al. | |
| 2010/0217304 A1 | 8/2010 | Angel et al. | |
| 2010/0234932 A1 | 9/2010 | Arbefeville | |
| 2010/0305604 A1 | 12/2010 | Pah | |
| 2010/0312268 A1 | 12/2010 | Belson | |
| 2011/0015716 A1 | 1/2011 | Silverman | |
| 2011/0022076 A1 | 1/2011 | Lashinski | |
| 2011/0125258 A1 | 5/2011 | Centola | |
| 2011/0257592 A1 | 10/2011 | Ventura et al. | |
| 2012/0083877 A1 | 4/2012 | Nguyen et al. | |
| 2012/0101510 A1 | 4/2012 | Lenker et al. | |
| 2012/0209375 A1 | 8/2012 | Madrid et al. | |
| 2013/0131787 A1 | 5/2013 | Ginn | |
| 2013/0138201 A1 | 5/2013 | Ginn | |
| 2014/0336695 A1 | 11/2014 | Naor | |
| 2014/0336752 A1 | 11/2014 | Ginn et al. | |
| 2016/0338828 A1 | 11/2016 | Ginn | |

FOREIGN PATENT DOCUMENTS

| | | |
|---|---|---|
| CA | 2855387 A1 | 5/2013 |
| CN | 1204242 A | 1/1999 |
| CN | 104039381 A | 9/2014 |
| EP | 2663355 A1 | 11/2013 |
| EP | 2776114 A1 | 9/2014 |
| EP | 3449969 A1 | 9/2014 |
| EP | 2776114 B1 | 10/2018 |
| FR | 2776114 A1 | 9/1999 |
| FR | 2776114 B1 | 10/2007 |
| JP | H09501594 A | 2/1997 |
| JP | H11509130 A | 8/1999 |
| JP | 2001517973 A | 10/2001 |
| JP | 2002336261 A | 11/2002 |
| JP | 2006500970 A | 1/2006 |
| JP | 2009529401 A | 8/2009 |
| JP | 2013-34867 A | 2/2013 |
| JP | 2015500681 A | 1/2015 |
| WO | 95/05207 A2 | 2/1995 |
| WO | 97/21403 A1 | 6/1997 |
| WO | 98/09678 A1 | 3/1998 |
| WO | 99/24102 A1 | 5/1999 |
| WO | 01/91844 A1 | 6/2001 |
| WO | 02/056955 | 7/2002 |
| WO | 02/056955 A1 | 7/2002 |
| WO | 03/090834 A2 | 11/2003 |
| WO | 2007/106755 A1 | 9/2007 |
| WO | 2009/131612 A1 | 10/2009 |
| WO | 2010/045297 A2 | 4/2010 |
| WO | 2010105195 A2 | 9/2010 |
| WO | 2011/096975 A1 | 11/2011 |
| WO | 2013/037505 | 3/2013 |
| WO | 2013037505 A1 | 3/2013 |
| WO | 2013071179 A1 | 5/2013 |

OTHER PUBLICATIONS

Extended European Search Report dated Oct. 28, 2016, International Patent Application No. PCT/US14/037924 with International Filing Date of May 13, 2014 (9 Pages).
"U.S. Appl. No. 13/673,898, Advisory Action dated Jul. 31, 2017", 3 pgs.
"U.S. Appl. No. 13/673,898, Advisory Action dated Aug. 5, 2016", 5 pgs.
"U.S. Appl. No. 13/673,898, Appeal Brief filed Jul. 19, 2017", 19 pgs.
"U.S. Appl. No. 13/673,898, Appeal Brief filed Aug. 9, 2017", 2 pgs.

(56) References Cited

OTHER PUBLICATIONS

"U.S. Appl. No. 13/673,898, Appeal Decision mailed Dec. 27, 2019", 26 pgs.
"U.S. Appl. No. 13/673,898, Examiner's Answer to Appeal Brief mailed Dec. 19, 2017", 12 pgs.
"U.S. Appl. No. 13/673,898, Final Office Action dated Apr. 20, 2017", 20 pgs.
"U.S. Appl. No. 13/673,898, Final Office Action dated May 25, 2016", 10 pgs.
"U.S. Appl. No. 13/673,898, Non Final Office Action dated Sep. 14, 2015", 11 pgs.
"U.S. Appl. No. 13/673,898, Non Final Office Action dated Nov. 16, 2016", 16 pgs.
"U.S. Appl. No. 13/673,898, Notice of Non-Complaint Appeal Brief mailed Aug. 2, 2017", 2 pgs.
"U.S. Appl. No. 13/673,898, Reply Brief filed Jan. 30, 2018", 9 pgs.
"U.S. Appl. No. 13/673,898, Response filed Feb. 5, 2016 to Non Final Office Action dated Sep. 14, 2015", 8 pgs.
"U.S. Appl. No. 13/673,898, Response filed Jun. 2, 2017 to Final Office Action dated Apr. 20, 2017", 6 pgs.
"U.S. Appl. No. 13/673,898, Response filed Jun. 14, 2016 to Final Office Action dated May 25, 2016", 10 pgs.
"U.S. Appl. No. 13/673,898, Response filed Aug. 7, 2015 to Restriction Requirement dated Mar. 20, 2015", 5 pgs.
"U.S. Appl. No. 13/673,898, Response filed Aug. 8, 2016 to Advisory Action dated Aug. 5, 2016", 10 pgs.
"U.S. Appl. No. 13/673,898, Response filed Dec. 22, 2016 to Non Final Office Action dated Nov. 16, 2016", 11 pgs.
"U.S. Appl. No. 13/673,898, Restriction Requirement dated Mar. 20, 2015", 6 pgs.
"U.S. Appl. No. 13/673,911, Advisory Action dated Feb. 16, 2016", 3 pgs.
"U.S. Appl. No. 13/673,911, Final Office Action dated Dec. 18, 2015", 6 pgs.
"U.S. Appl. No. 13/673,911, Non Final Office Action dated Apr. 6, 2015", 11 pgs.
"U.S. Appl. No. 13/673,911, Notice of Allowance dated Mar. 11, 2016", 9 pgs.
"U.S. Appl. No. 13/673,911, Response filed Jan. 28, 2016 to Final Office Action dated Dec. 18, 2015", 8 pgs.
"U.S. Appl. No. 13/673,911, Response filed Mar. 1, 2016 to Advisory Action dated Feb. 16, 2016", 7 pgs.
"U.S. Appl. No. 13/673,911, Response filed Sep. 8, 2015 to Non Final Office Action dated Apr. 4, 2015", 7 pgs.
"U.S. Appl. No. 14/274,563, 312 Amendment filed Aug. 9, 2016", 4 pgs.
"U.S. Appl. No. 14/274,563, 312 Amendment filed Aug. 12, 2016", 3 pgs.
"U.S. Appl. No. 14/274,563, Advisory Action dated Jun. 3, 2016", 3 pgs.
"U.S. Appl. No. 14/274,563, Final Office Action dated Mar. 28, 2016", 19 pgs.
"U.S. Appl. No. 14/274,563, Non Final Office Action dated Jun. 3, 2015", 15 pgs.
"U.S. Appl. No. 14/274,563, Non Final Office Action dated Sep. 8, 2014", 7 pgs.
"U.S. Appl. No. 14/274,563, Notice of Allowance dated Aug. 8, 2016", 11 pgs.
"U.S. Appl. No. 14/274,563, PTO Response to Rule 312 Communication dated Sep. 26, 2016", 2 pgs.
"U.S. Appl. No. 14/274,563, Response filed Feb. 9, 2015 to Non Final Office Action dated Sep. 8, 2014", 13 pgs.
"U.S. Appl. No. 14/274,563, Response filed Apr. 29, 2016 to Final Office Action dated Mar. 28, 2016", 9 pgs.
"U.S. Appl. No. 14/274,563, Response filed Jun. 15, 2016 to Advisory Action dated Jun. 3, 2016", 9 pgs.
"U.S. Appl. No. 14/274,563, Response filed Oct. 20, 2015 to Non Final Office Action dated Jun. 3, 2015", 11 pgs.
"U.S. Appl. No. 15/228,380, Final Office Action dated Nov. 14, 2018", 8 pgs.
"U.S. Appl. No. 15/228,380, Non Final Office Action dated Apr. 20, 2018", 7 pgs.
"U.S. Appl. No. 15/228,380, Non Final Office Action dated Jun. 26, 2019", 8 pgs.
"U.S. Appl. No. 15/228,380, Response filed Feb. 14, 2019 to Final Office Action dated Nov. 14, 2018", 6 pgs.
"U.S. Appl. No. 15/228,380, Response filed Jun. 26, 2018 to Non Final Office Action dated Apr. 20, 2018", 7 pgs.
"U.S. Appl. No. 15/228,380, Response filed Oct. 24, 2019 to Non-Final Office Action dated Jun. 26, 2019", 7 pgs.
"Australian Application Serial No. 2012335016, First Examiner Report dated Jul. 17, 2016", 3 pgs.
"Australian Application Serial No. 2012335016, Response filed Jan. 12, 2017 to First Examiner Report dated Jul. 17, 2016", 17 pgs.
"Australian Application Serial No. 2012335016, Response filed Apr. 12, 2017 to Second Examiner Report dated Feb. 20, 2017", 8 pgs.
"Australian Application Serial No. 2012335016, Response filed Jun. 29, 2017 to Third Examiner Report dated Jun. 12, 2017", 11 pgs.
"Australian Application Serial No. 2012335016, Second Examiner Report dated Feb. 20, 2017", 3 pgs.
"Australian Application Serial No. 2012335016, Third Examiner Report dated Jun. 12, 2017", 4 pgs.
"Canadian Application Serial No. 2,855,387, Office Action dated Jun. 12, 2018", 4 pgs.
"Canadian Application Serial No. 2,855,387, Office Action dated Mar. 8, 2019", 4 pgs.
"Canadian Application Serial No. 2,855,387, Response filed Sep. 6, 2019 to Office Action dated Mar. 8, 2019", 78 pgs.
"Canadian Application Serial No. 2,855,387, Response filed Dec. 12, 2018 to Office Action dated Jun. 12, 2018", 27 pgs.
"Canadian Application Serial No. 2,855,387, Voluntary Amendment filed Oct. 29, 2019", 14 pgs.
"Chinese Application Serial No. 201280066517.X, Office Action dated Oct. 26, 2015", 17 pgs.
"European Application Serial No. 12847961.5, Communication Pursuant to Article 94(3) EPC dated Mar. 29, 2016", 5 pgs.
"European Application Serial No. 12847961.5, Communication Pursuant to Article 94(3) EPC dated Aug. 17, 2017", 6 pgs.
"European Application Serial No. 12847961.5, Communication Pursuant to Article 94(3) EPC dated Nov. 15, 2016", 5 pgs.
"European Application Serial No. 12847961.5, Extended European Search Report dated May 22, 2015", 8 pgs.
"European Application Serial No. 12847961.5, Intention to Grant dated Apr. 26, 2018", 95 pgs.
"European Application Serial No. 12847961.5, Intention to Grant dated Sep. 17, 2018", 95 pgs.
"European Application Serial No. 12847961.5, Response filed Jan. 2, 2015 to Communication Pursuant to Rules 161(1) and 162 EPC dated Jun. 23, 2014", 11 pgs.
"European Application Serial No. 12847961.5, Response filed May 24, 2017 to Communication Pursuant to Article 94(3) EPC dated Nov. 15, 2016", 52 pgs.
"European Application Serial No. 12847961.5, Response filed Sep. 5, 2018 to Intention to Grant dated Apr. 26, 2018", 8 pgs.
"European Application Serial No. 12847961.5, Response filed Oct. 10, 2016 to Communication Pursuant to Article 94(3) EPC dated Mar. 29, 2016", 13 pgs.
"European Application Serial No. 12847961.5, Response filed Dec. 21, 2015 to Extended European Search Report dated May 22, 2015", 12 pgs.
"European Application Serial No. 12847961.5, Response filed Dec. 29, 2017 to Communication Pursuant to Article 94(3) EPC dated Aug. 17, 2017", 52 pgs.
"European Application Serial No. 18201608.9, Extended European Search Report dated Feb. 1, 2019", 10 pgs.
"International Application Serial No. PCT/US2012/064540, International Preliminary Report on Patentability dated May 22, 2014", 11 pgs.
"International Application Serial No. PCT/US2012/064540, International Search Report dated Feb. 6, 2013", 2 pgs.
"International Application Serial No. PCT/US2012/064540, Written Opinion dated Feb. 6, 2013", 9 pgs.

(56) References Cited

OTHER PUBLICATIONS

"International Application Serial No. PCT/US2014/037580, International Preliminary Report on Patentability dated Nov. 19, 2015", 8 pgs.

"Israel Application Serial No. 232542, Office Action dated Sep. 4, 2018", w/o English Translation, 5 pgs.

"Israel Application Serial No. 232542, Office Action dated Sep. 18, 2017", w/o English Translation, 3 pgs.

"Israel Application Serial No. 232542, Response filed Jan. 18, 2018 to Office Action dated Sep. 18, 2017", 2 pgs.

"Israel Application Serial No. 232542, Response filed Dec. 16, 2018 to Office Action dated Sep. 4, 2018", 2 pgs.

"Japanese Application Serial No. 2014-541354, Notice of Reason for Rejection dated Jul. 28, 2016", w/ English Translation, 22 pgs.

EP Application No. 20200790.2, Extended European Search Report, dated Feb. 5, 2021, 7 pages.

JP Application No. 2020-038658, Japanese Office Action, dated Sep. 27, 2021, 4 pages.

\* cited by examiner

US 11,234,845 B2

EXPANDABLE INTRODUCER SHEATH

RELATED APPLICATION DATA

The present application is a continuation-in-part of U.S. patent application Ser. No. 13/673,898, filed on Nov. 9, 2012 and entitled "System for Deploying a Device to a Distal Location Across a Diseased Vessel"; U.S. patent application Ser. No. 13/673,911, filed on Nov. 9, 2012 and entitled "Method for Deploying a Device to a Distal Location Across a Diseased Vessel; each of which claims the benefit of U.S. Provisional Patent Application Ser. No. 61/717,575, filed Oct. 23, 2012 and entitled "System for Deploying a Device to a Distal Location Across a Diseased Vessel"; U.S. Provisional Patent Application Ser. No. 61/558,397, filed Nov. 10, 2011 and entitled "System for Deploying a Device to a Distal Location Across a Diseased Vessel"; U.S. Provisional Patent Application Ser. No. 61/558,357, filed Nov. 10, 2011 and entitled "Method for Deploying a Device to a Distal Location Across a Diseased Vessel. The Present application is also a continuation-in-part of U.S. patent application Ser. No. 14/274,563, filed May 9, 2014 and entitled "System for Deploying a Device to a Distal Location Across a Diseased Vessel"; which claims the benefit of U.S. Provisional Patent Application Ser. No. 61/822,204, filed May 10, 2013 and entitled "System for Deploying a Device to a Distal Location Across a Diseased Vessel", all of which are hereby incorporated by reference herein.

FIELD OF THE INVENTION

The present invention relates generally to medical interventions conducted through vessels such as the major arteries, and more particularly to access and deployment configurations for conducting percutaneous procedures such as percutaneous valve replacement wherein an introducer sheath may be utilized to provide minimally-invasive vascular access for passing instruments, prostheses, and other structures.

BACKGROUND

Gaining access to the heart and other parts of the cardiovascular anatomy is a continued challenge in cardiovascular medicine. For example, conventional open-surgical procedures for accomplishing tasks such as valve replacement generally involve a thoracotomy and/or creation of one or more access ports across the wall of the heart itself, which is relatively highly invasive and therefore undesirable. Recent progress has been made in the area of catheter-based percutaneous intervention, wherein instrumentation, such as catheters, guidewires, and prostheses, are brought to the heart, brain, or other tissue structures associated with the cardiovascular system through the vessels connected to such structures. These vascular pathways may be quite tortuous and geometrically small, and thus one of the challenges with percutaneous procedures lies in gaining access, conducting the desired interventional and/or diagnostic procedures, and removing the pertinent instrumentation, without damaging the vasculature or associated anatomy. Conventionally with percutaneous procedures, introducer and dilator sets such as that (2) depicted in FIG. 1, have been utilized to provide a usable access conduit through an arteriotomy or other surgical access to the vasculature. For procedures on large, relatively straight, and relatively undiseased vessels, such configurations may be adequate, but frequently cardiovascular diagnostic and/or interventional procedures are conducted on diseased cardiovascular systems and in tortuous anatomy. There is a need for better access tools and procedures, which may be utilized to establish vascular access in a relatively efficient geometric package (i.e., in a collapsed state), be expanded in situ as necessary to pass instrumentation, prostheses, or other structures (for example, the un-expanded delivery size of a CoreValve® aortic valve prosthesis available from Medtronic, Inc. is approximately 18 French; the un-expanded delivery size of a Sapien® valve available from Edwards Lifesciences, Inc. is between 18 and 24 French, depending upon which size is utilized), and to be re-collapsed before or during withdrawal so that the associated anatomy is not undesirably loaded or damaged during such withdrawal. Various embodiments of the subject invention address these challenges with expandable introducer sheath configurations.

SUMMARY

One embodiment is directed to a system for deploying a device to a distal location across a vessel, comprising an elongate introducer sheath tubing member comprising open-cell fibrous wall material defining a lumen therethrough, wherein in a collapsed configuration the sheath has a first cross-sectional outer diameter and a first lumen inner diameter, and in an expanded configuration, the sheath has a second cross-sectional outer diameter and a second lumen inner diameter; and a substantially non-porous expandable layer coupled to a proximal portion of sheath and configured to prevent fluids present in the lumen from crossing the fibrous wall material. In the collapsed configuration, the sheath may be configured to be advanced across at least a portion of the vessel to a position adjacent the distal location without substantial size interference between the first cross sectional outer diameter of the sheath and an inner diameter profile of a lumen of the vessel. Upon positioning the collapsed configuration to the desired position relative to the distal location, the sheath may be configured to be expanded to the expanded configuration to facilitate passage of one or more relatively large diameter structures through the lumen that are larger in diameter than the first cross sectional outer diameter. Upon completion of passage of the one or more relatively large diameter structures, the sheath may be configured to be collapsed back to the collapsed configuration. The first lumen inner diameter may be equal to between about 0 mm and about 4 mm. The second lumen inner diameter may be equal to between about 4 mm and about 7 mm. The system further may comprise one or more radio-opaque markers coupled to the sheath and configured to assist an operator observing fluoroscopy with positioning of the sheath relative to the vessel. The open-cell fibrous wall material may comprise a matrix of fibers. The matrix of fibers may be arranged in a braided pattern. The fibers may comprise a polymeric material. The polymeric material may be selected from the group consisting of: polyester, polyamide, polypropylene, and copolymers thereof. The fibers each may have a diameter of between about 0.003 inches and about 0.015 inches. The matrix of fibers may be configured to function to prevent expansion of the sheath beyond the second cross-sectional outer diameter. The matrix of fibers may be configured to bias the sheath to remain in the collapsed configuration until it is urged into the expanded configuration by passage of a structure through the lumen. The matrix of fibers may be configured to locally expand around the structure passed through the lumen, and then to locally re-collapse as the structure passes to an adjacent portion of the lumen. The substantially non-porous expandable layer may comprise a flexible polymeric material selected from the group consisting of: silicone rubber, olefin block copolymers, and copolymers thereof. The matrix of fibers may define pores across the wall material which have a diameter between about 0.002 inches and about 0.20 inches. The system further may comprise an inner liner member operatively coupled through the lumen of the elongate introducer sheath tubing member to define an inner working lumen, the inner liner member configured to structurally reinforce the tubing member and facilitate relative motion between structures which maybe passed through the inner working lumen. The substantially non-porous expandable layer may be configured to extend from a proximal end of the elongate introducer sheath tubing member for a length of about 10 centimeters distally. The device may comprise an implantable prosthesis selected to be passed through the expandable sheath to the distal location across the vessel. The implantable prosthesis may comprise a cardiac valve prosthesis. The matrix of fibers may comprise a mesh pattern. The system further may comprise a tensioning member operatively coupled to at least a portion of the matrix of fibers and configured to maintain such portion in a relaxed configuration, the tensioning member comprising a proximal portion configured to be manually tensioned or relaxed by an operator.

DETAILED DESCRIPTION

Figure 1:
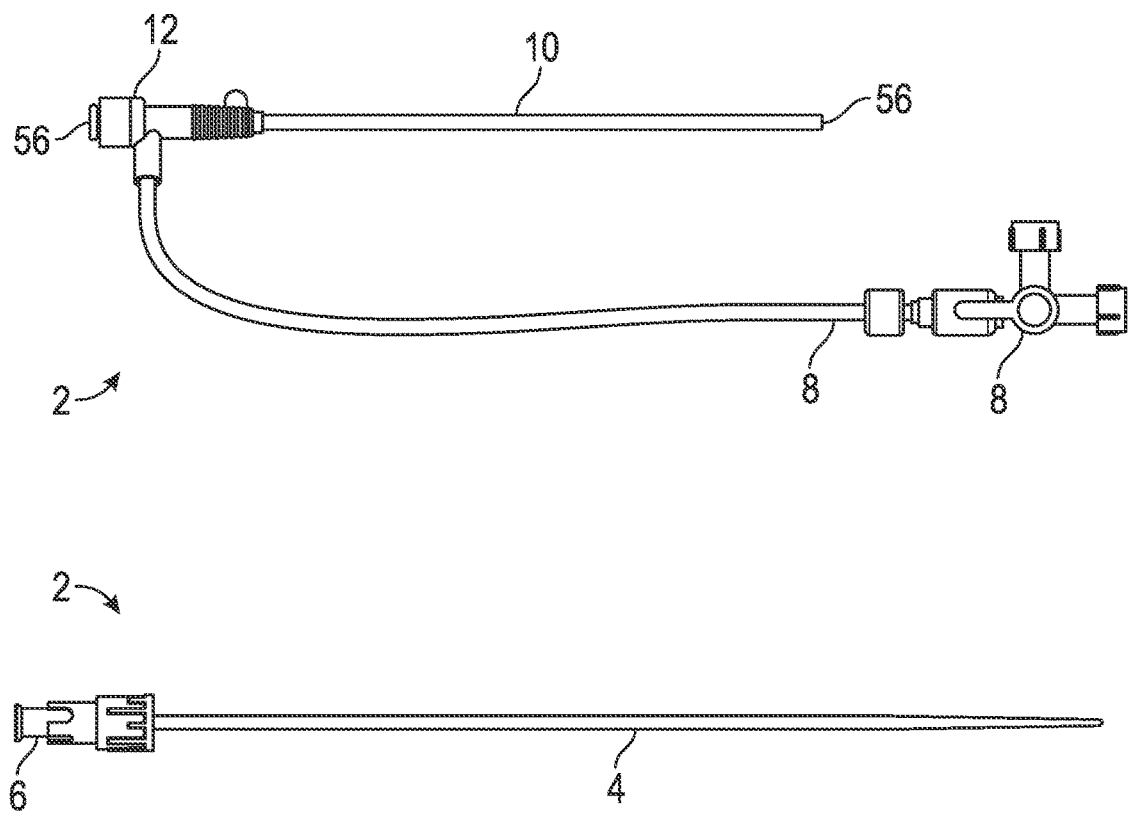
FIG. 1 illustrates various aspects of a conventional introducer and dilator kit for cardiovascular intervention.

Referring again to FIG. 1, a conventional introducer sheath and dilator kit (2) is depicted comprising an elongate dilator (4) with a proximal Luer assembly (6); the dilator is configured to be inserted into the working lumen (56) of the introducer sheath through a proximal seal coupled to a hub (12) structure, which is also coupled to an extension tube with stopcock (8), which may be utilized for infusion of fluids into the introducer lumen (56), for example. The conventional introducer sheath will comprise an elongate tubular member (10) coupled proximally to the hub (12) and being made from a relatively non-expandable polymeric material or combination of polymeric materials, which results in introducer sheaths which are selected for their off-the-shelf working lumen (56) diameter (i.e., they generally are not considered to have expandable diametric dimensions). Certain trocars and introducer catheters have been produced with expandable diametric geometries, but they have been limited in their expandability due to the constraints of hoop stress and friction (i.e., with a relatively low-modulus or even rubber-like material, diametric expansion will be at least linearly proportional to hoop stress in the expanded sheath material, which is proportional to frictional loads—which generally results in a useful expandability limit, beyond which too large a load is required to develop relative motion between structures being passed through the working lumen and the sheath which defines the working lumen).

Figure 2A:
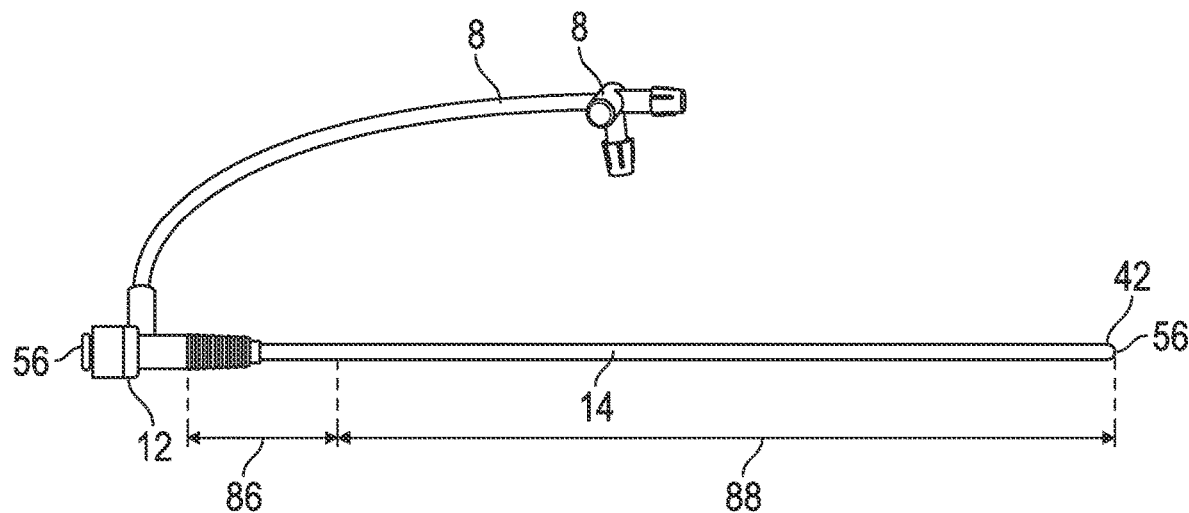
FIGS. 2A-2O illustrate various aspects of an inventive expandable introducer sheath that may be used in conducting various cardiovascular procedures.

Referring to FIG. 2A, one embodiment of an expandable introducer sheath to address these challenges is depicted, wherein the introducer sheath tubing member or assembly (14) comprises a plurality of braided fibers arranged in a braided or mesh pattern to form an open-cell fibrous wall material comprising the sheath tubing member, which defines the introducer working lumen (56). In one embodiment the distal portion (88) of the introducer sheath tubing member (14) comprises the open-cell fibrous wall material in its porous form without a nonporous coating, while a portion of the proximal portion (86), such as about the proximal 10 centimeters, of the introducer sheath tubing member (14) is coated with a substantially non-porous expandable layer to assist with preventing bleeding when the sheath is installed in a patient with the proximal portion extending transcutaneously out of the surgically-created wound (such as an arteriotomy).

Figure 2B:
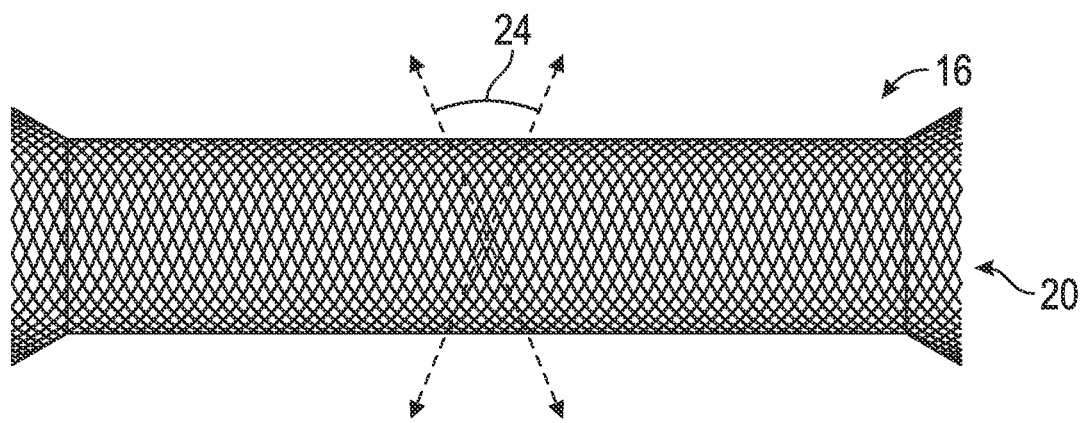
Figure 2C:
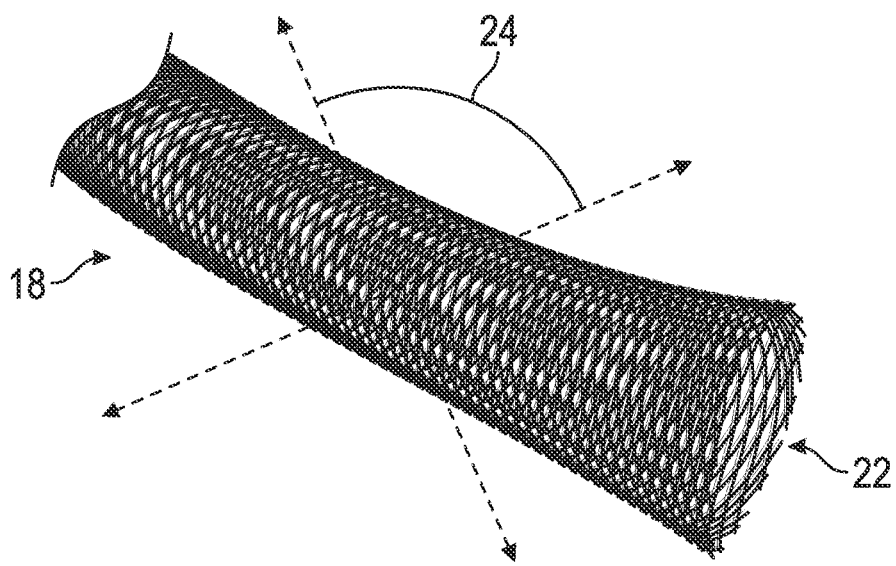
Figure 2D:
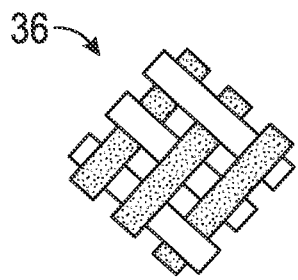
Figure 2E:
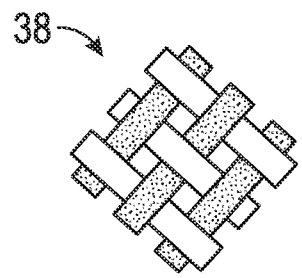
Figure 2F:
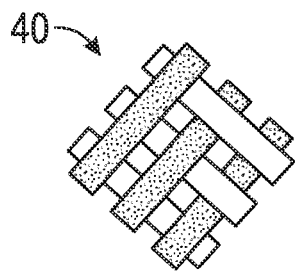

Referring to FIG. 2B, a braiding configuration (16) is depicted wherein single strands (20) of fibrous material are braided with each other, such as in one of the depicted patterns of FIG. 2D, 2E, or 2F (36, 38, or 40, respectively) to allow for significant diametric expandability and contractability of the overall fiber/mesh assembly due to available relative motion between the fibers in an open-cell braided configuration. In other words, it is the available micromotion of the fibers of the braided pattern relative to each other that allows for relatively low-load expandability and contractability of the overall construct. This relative motion may be somewhat decreased when the fibrous assembly is combined with other structures, such as a nonporous coating, which is the reason that in one embodiment, wherein maximum expandability and contractability is preferred, such nonporous coating is only featured on the proximal aspect, or in another embodiment, not at all (i.e., there is no nonporous coating in such embodiment, and proximal bleed-through at the percutaneous access site may be mitigated by another means such as gauze compression or a very thin and highly-expandable lubricious sleeve that is not directly coupled to each portion of the surface of the braided assembly, but is essentially looped around the bulk structure only with a light hoop stress). The intersection angle (24) of intersecting fibers within the woven, braided, or mesh pattern will change with collapse or expansion of the overall structure, and may be selected to affirmatively limit the lower bounds of collapse diameter, as well as the upper bounds of expansion diameter.

FIG. 2C depicts another braiding assembly (18) wherein each of the braided fibers actually comprises a plurality of parallel fibers grouped together (22); the pattern of FIG. 2C has groups of approximately three small fibers travelling the woven, braided, or meshed pattern together.

In one embodiment, the fibers may comprise a polymeric material such as polyester, polyamide, polypropylene, or copolymers thereof. In one embodiment the fibers each may have a cross sectional diameter of between about 0.003 inches and about 0.015 inches. In one embodiment the braiding, mesh, or weave pattern may produce pores in the expandable sheath wall material which have a diameter between about 0.002 inches and about 0.20 inches. In one embodiment a nonporous coating layer on the proximal portion of the expandable sheath assembly may comprise a flexible polymeric material such as silicone rubber, olefin block copolymers, and/or copolymers thereof.

Figure 2G:
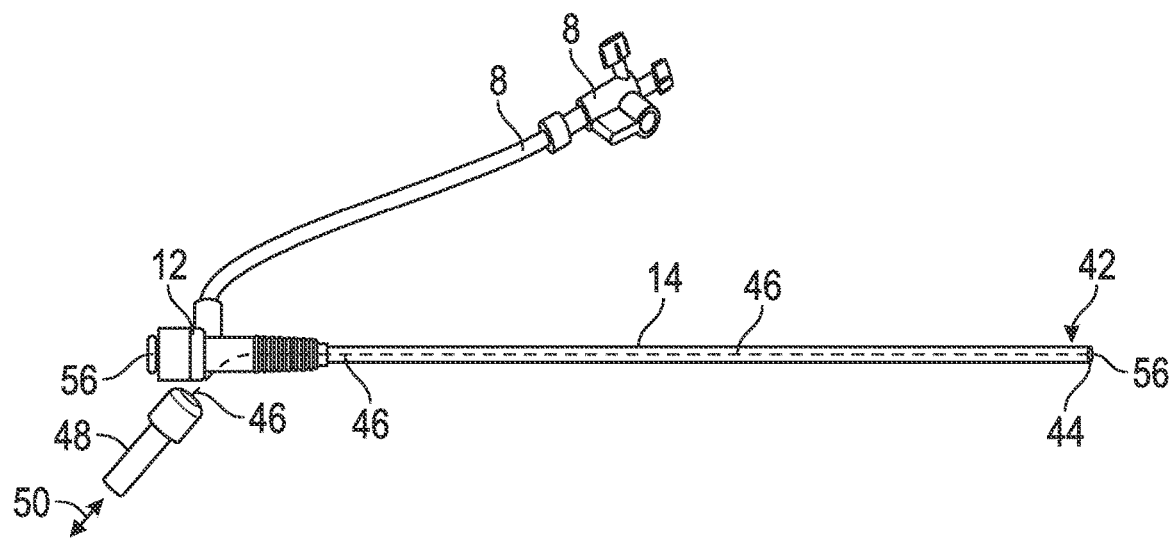

When either of the braided fiber assemblies (16, 18) are tensioned (i.e., from either end), they will decrease in overall geometry as the fibers comprising such assemblies move relative to each other; similarly, when such assemblies are compressed, they will increase in overall geometry. This factor may be controllably utilized to assist with delivery and use of the subject elongate instrument. For example, referring to FIG. 2G, in one embodiment, an elongate loading member (46), such as a pullwire or pushwire (which may also be called a pushrod), may be operatively coupled between the distal end (42) of the introducer sheath tubing member (14), such as by direct mechanical coupling to a distal ring member (44) coupled to the distal tip (42) of the introducer sheath tubing member (14) and proximal coupling to a proximal control interface (48) such as a pull or push handle configured to allow an operator to manually apply tensile or compressive loads (50) to the elongate loading member (46). Such a coupling configuration allows for manually-actuated and controlled expansion or contraction of the introducer sheath tubing member (14) from a proximal location. Referring ahead to FIG. 2N, other associated structures, such as a dilator assembly or portions thereof, and/or a temporary locking member (80), may be utilized to place an introducer sheath tubing member (14) into a sustained tensile loading configuration (FIG. 2N illustrates an embodiment utilizing a locking member 80 to lock two portions of a dilator assembly (an inner dilator member 64 and an outer dilator member 66) into a loading configuration against each other, with the inner dilator member in tension and outer dilator member in compression, such that a distal portion of the sheath tubing member 14 remains intercoupled in between such dilator members 64, 66, and such that the introducer sheath tubing member 14 may be actively and sustainably pulled into tension to retain a decreased cross sectional diameter until the locking member 80 is removed) to assist with insertion or removal of the introducer sheath tubing member (14) relative to the associated anatomy.

Figure 2H:
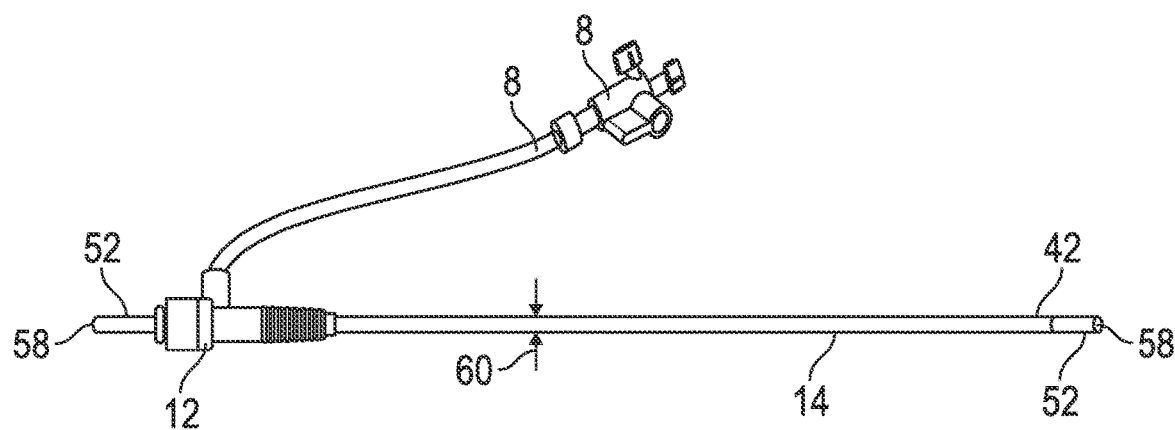
Figure 2I:
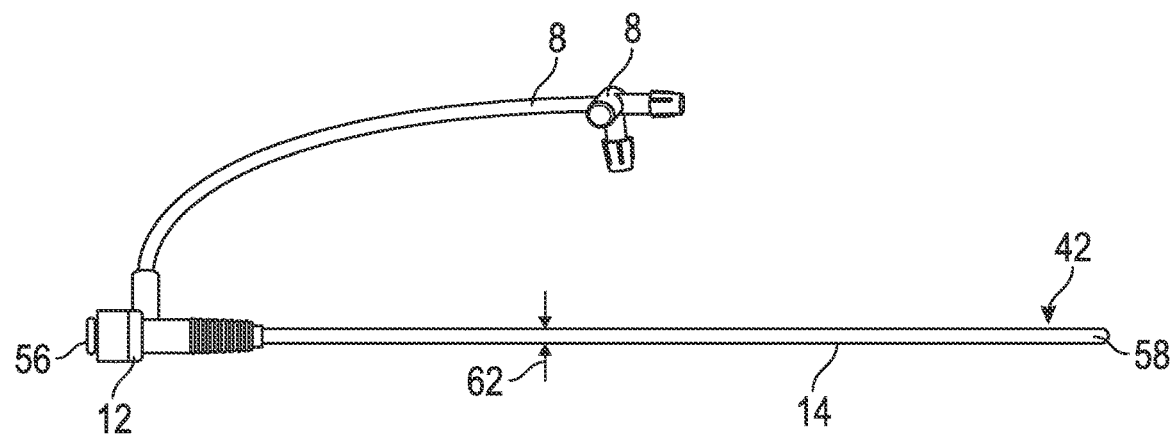

Referring to FIG. 2H, in another embodiment, it may be desirable to insert a tubular liner member (52), such as a polymeric tubular member, defining a tubular liner member lumen therethrough, to assist with insertion and/or withdrawal of structures through the introducer sheath tubing member (14). The tubular liner member may be selected to have a higher structural modulus than that of the introducer sheath tubing member (14) to effectively provide some rigidity and kink resistance to the overall assembly. The inner diameter of the tubular liner member (52) preferably will be sized to define a working lumen therethrough that will accommodate selected instrumentation without substantial expansion of the tubular liner member (52), and insertion of the tubular liner member (52) generally will urge the associated introducer sheath tubing member (14) from a relatively collapsed configuration to a relatively expanded configuration; removal of the tubular liner member will allow the introducer sheath tubing member (14) to return to the relatively collapsed configuration; this is demonstrated in the difference in outer diameters (60, 62) of the depicted introducer sheath tubing member (14) in FIG. 2H with the tubular liner member (52) in place urging the introducer sheath tubing member (14) to the more expanded configuration, and FIG. 2I with the tubular liner member removed, allowing the introducer sheath tubing member (14) to return to the relatively collapsed configuration.

Figure 2J:
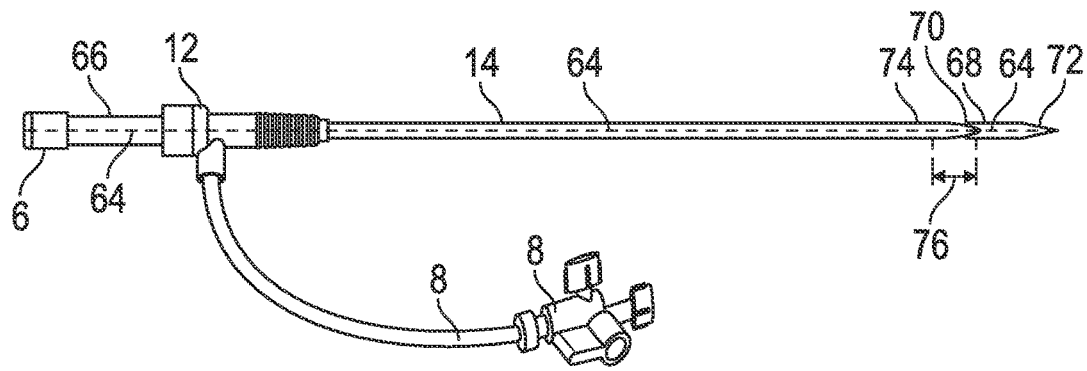

Referring to FIG. 2J, an assembly is shown utilizing an introducer sheath tubing member (14) along with other structures in a cardiovascular access configuration. In this embodiment, a two-part dilator assembly is used, as described above in reference to FIG. 2N. The assembly comprises an inner dilator assembly (comprised of an inner elongate dilator member 64 fixedly coupled to a distal dilator tip 68 having a tapered distal portion 72; the proximal portion of the inner elongate dilator member is fitted through the seal of the hub 12 and coupled proximally to a Luer assembly 6) movably coupled to an outer elongate dilator member (66). This dilator assembly is fitted through the hub (12) and through the introducer sheath tubing member (14), with the exception of the tapered distal portion (74) of the introducer sheath tubing member (14), which is coupled into a tapered recessed inner geometry (70) of the proximal aspect of the dilator tip member (68) in a slightly compressed manner. As described above and further below in reference to FIG. 2N, with the distal portion of the sheath tubing member (14) intercoupled between the inverse taper (70) of the dilator tip member (68) and the tapered distal portion (78) of the outer dilator member (66), the sheath tubing member (14) may be tensioned to reduce cross sectional geometry by further inserting the outer dilator member (66) while the distal portion of the sheath tubing member (14) remains pinched and therefore coupled between the dilator tip member (68) and tapered end portion (78) of the outer dilator member (66); without this pinching constraint, the distal portion of the sheath tubing member (14) may be allowed to freely escape from the dilator tip member (68).

Figure 2K:
Figure 2L:
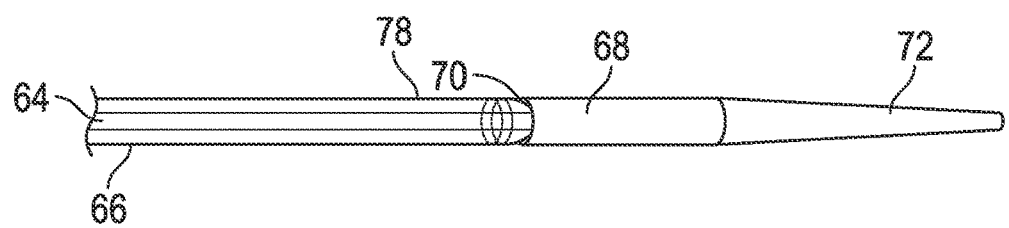
Figure 2M:
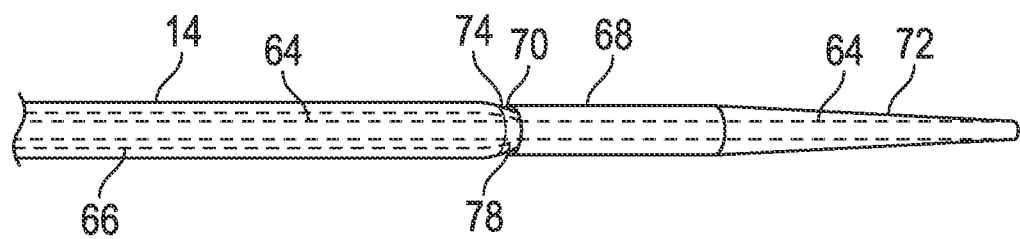
Figure 2N:
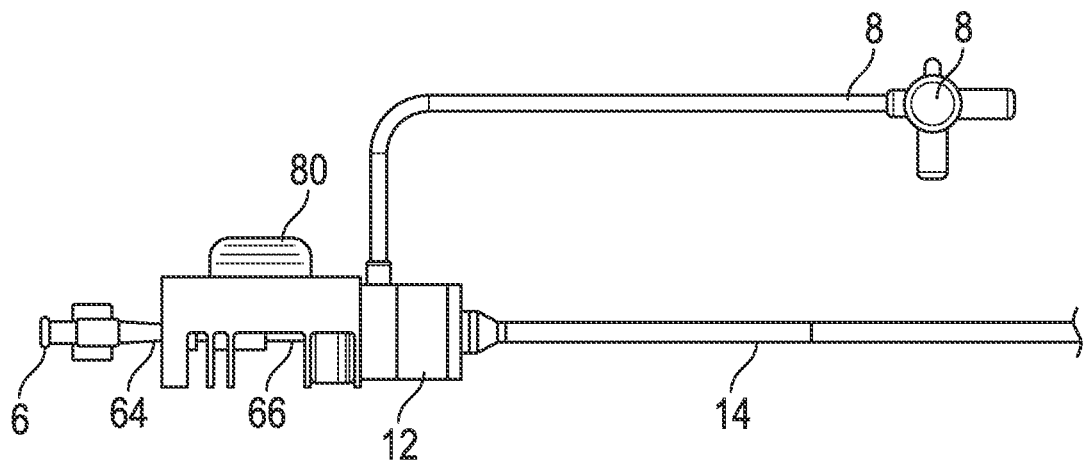

FIG. 2K illustrates an inner dilator assembly comprising an inner elongate dilator member (64) coupled to a dilator tip member (68) having a tapered distal portion (72) and a tapered proximal interior surface (70) for retrainably coupling with another tapered member which may be inserted into it, such as the distally tapered (78) outer dilator member (66) of FIG. 2L, or the distally tapered (74) introducer sheath tubing member (14) of FIG. 2M. FIG. 2M also illustrates that the outer dilator member (66—shown in dashed) may be inserted through the lumen of the introducer sheath tubing member (14) to capture a distal portion of the introducer sheath tubing member (14) in a pinched coupling manner between the outer dilator member (66) and the dilator tip member (68) which is coupled to the inner dilator member (64—also dashed), as described in reference to FIG. 2N.

As described above, FIG. 2N illustrates that a locking member (80) may be temporarily positioned between the hub (12) and a proximal portion of a dilator member (64) to place an introducer sheath tubing member (14) in tension between the hub (12) and dilator tip (68) to reduce the overall cross-sectional geometry of the introducer sheath tubing member (14) for improved insertion/withdrawal performance.

Figure 2O:
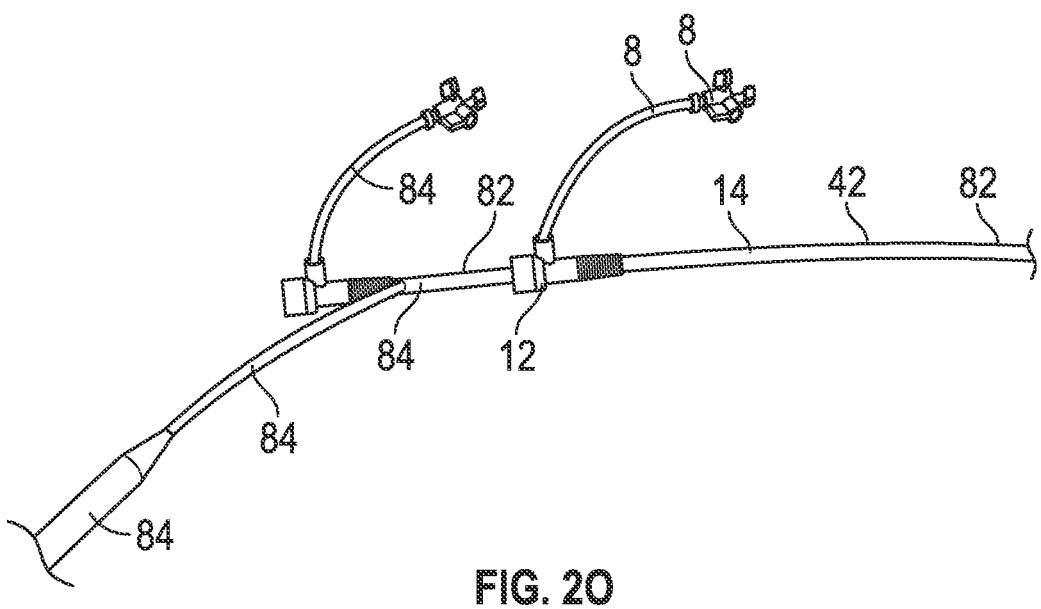

Referring to FIG. 2O, an interventional assembly (84), such as variations described in U.S. Patent Application Ser. No. 61/822,204, incorporated by reference herein in its entirety, the assembly (84) comprising an elongate tubular member (82), may be utilized with an introducer sheath tubing member (14) as described herein.

Referring to FIGS. 3-12, various configurations for procedures utilizing an expandable introducer sheath such as those described above are illustrated.

Figure 3:
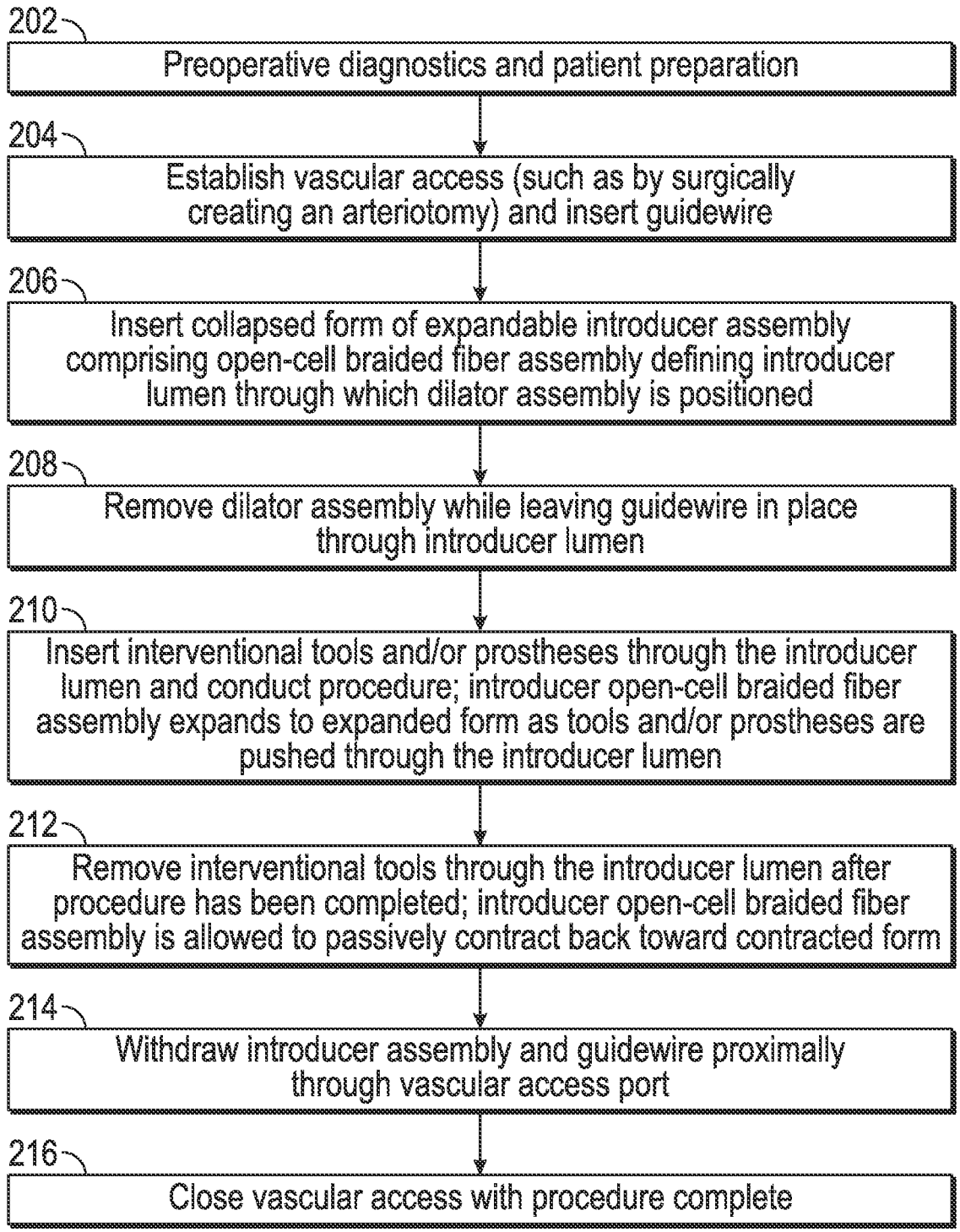
FIG. 3 illustrates various aspects of a minimally invasive surgical access technique in accordance with the present invention.

Referring to FIG. 3, after preoperative diagnostics and patient preparation (202), vascular access may be established, such as by a surgically-created arteriotomy cut-down, and a guidewire may be inserted (204), such as an 0.035" diameter guidewire. A collapsed form (i.e., with a first inner lumen diameter of between about 0 mm and about 4 mm) of an expandable introducer assembly comprising an open-cell braided fiber tube or tubular assembly may be inserted (206). In one embodiment the expandable fiber assembly may be expanded to provide inner working lumen diameters of between about 4 mm and about 7 mm, for example. With the tubular introducer sheath assembly in place, the associated dilator assembly may be removed (208). In one embodiment this may be accomplished by advancing the distal portion of the dilator assembly relative to the intercoupled braided expandable sheath to release the distal end of the expandable sheath from tension between the dilator distal portion and the hub (as described above in reference to FIG. 2N), allowing it to expand to provide an inner diameter sufficient to allow the dilator distal portion to be proximally withdrawn through the working lumen/inner diameter of the expandable sheath. At such point, the expandable sheath is in place relatively unconstrained, and the guidewire remains in place through the working lumen of the expandable sheath. In one embodiment one or more radio-opaque markers may be coupled to the expandable sheath assembly to assist with imaging confirmation of deployment location. Referring again to FIG. 3, interventional and/or diagnostic tools and/or prostheses may be inserted through the expandable sheath, thereby further expanding the sheath (210). Expansion of the expandable sheath may be localized, such that after a relatively large member is passed through and past a given portion of the sheath, that portion re-collapses, at least partially. After utilization of the interventional and/or diagnostic tools has been completed, they may be withdrawn proximally until there are removed, and the expandable sheath may be allowed to further collapse or contract in diameter (212). Subsequently the collapsed expandable sheath and guidewire may be proximally withdrawn (214) and the surgical access closed (216).

Figure 4:
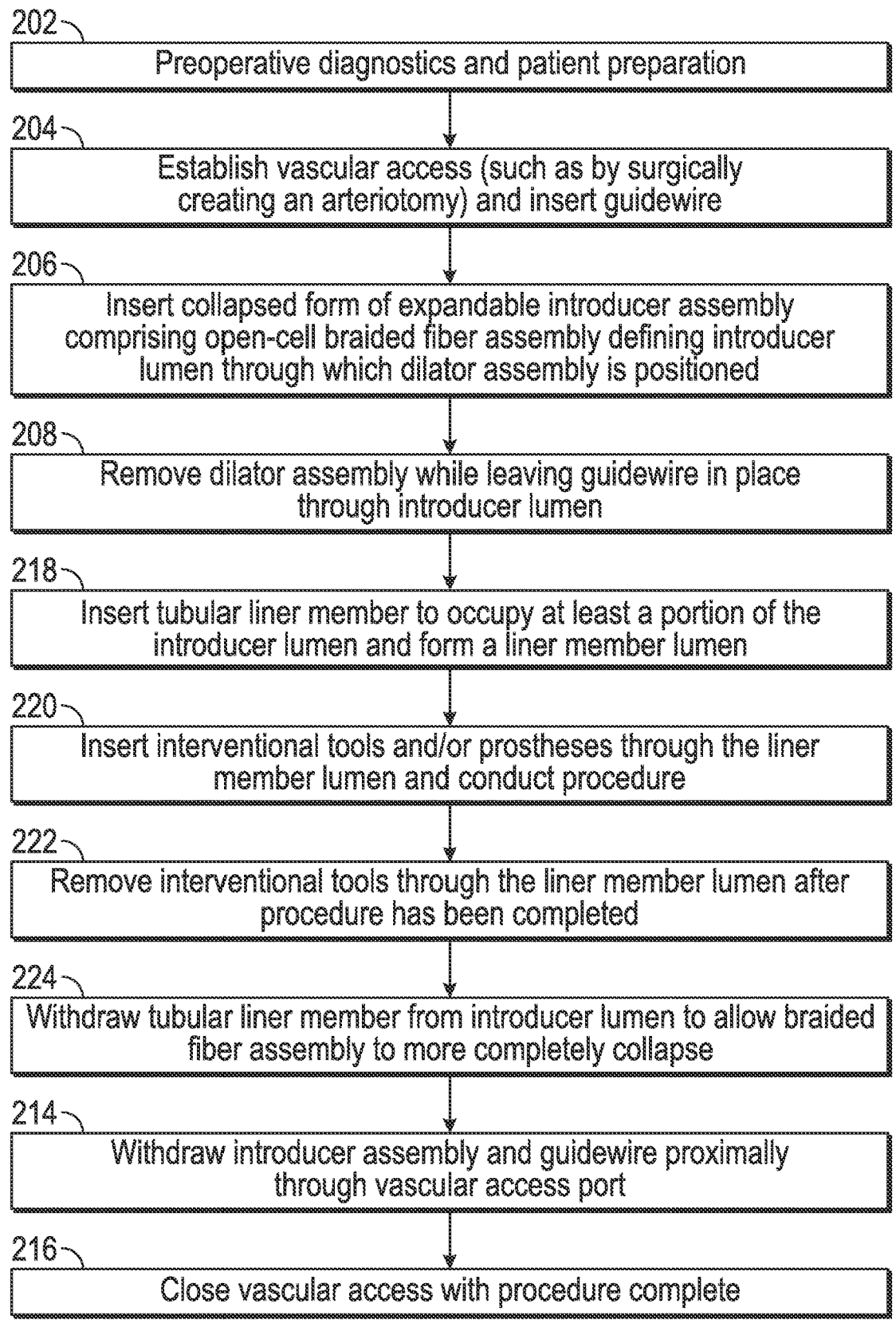
FIG. 4 illustrates various aspects of a minimally invasive surgical access technique in accordance with the present invention.

Referring to FIG. 4, an embodiment similar to that of FIG. 3 is depicted, with the exception that steps 210 and 212 of the embodiment of FIG. 3 have been replaced with steps 218, 220, 222, and 224, wherein a tubular liner is inserted to occupy at least a portion of the expandable introducer lumen, and to form a lumen within the liner which may be utilized as the new working lumen (218); tools for interventional and/or diagnostic procedure steps may be inserted through the liner lumen while the procedure is conducted (220); after the procedure has been completed the tools may be withdrawn out through the liner lumen (222), and subsequently the tubular liner itself may be withdrawn (224) to allow the expandable sheath to form a more collapsed geometry for withdrawal of such expandable sheath (214).

Figure 5:
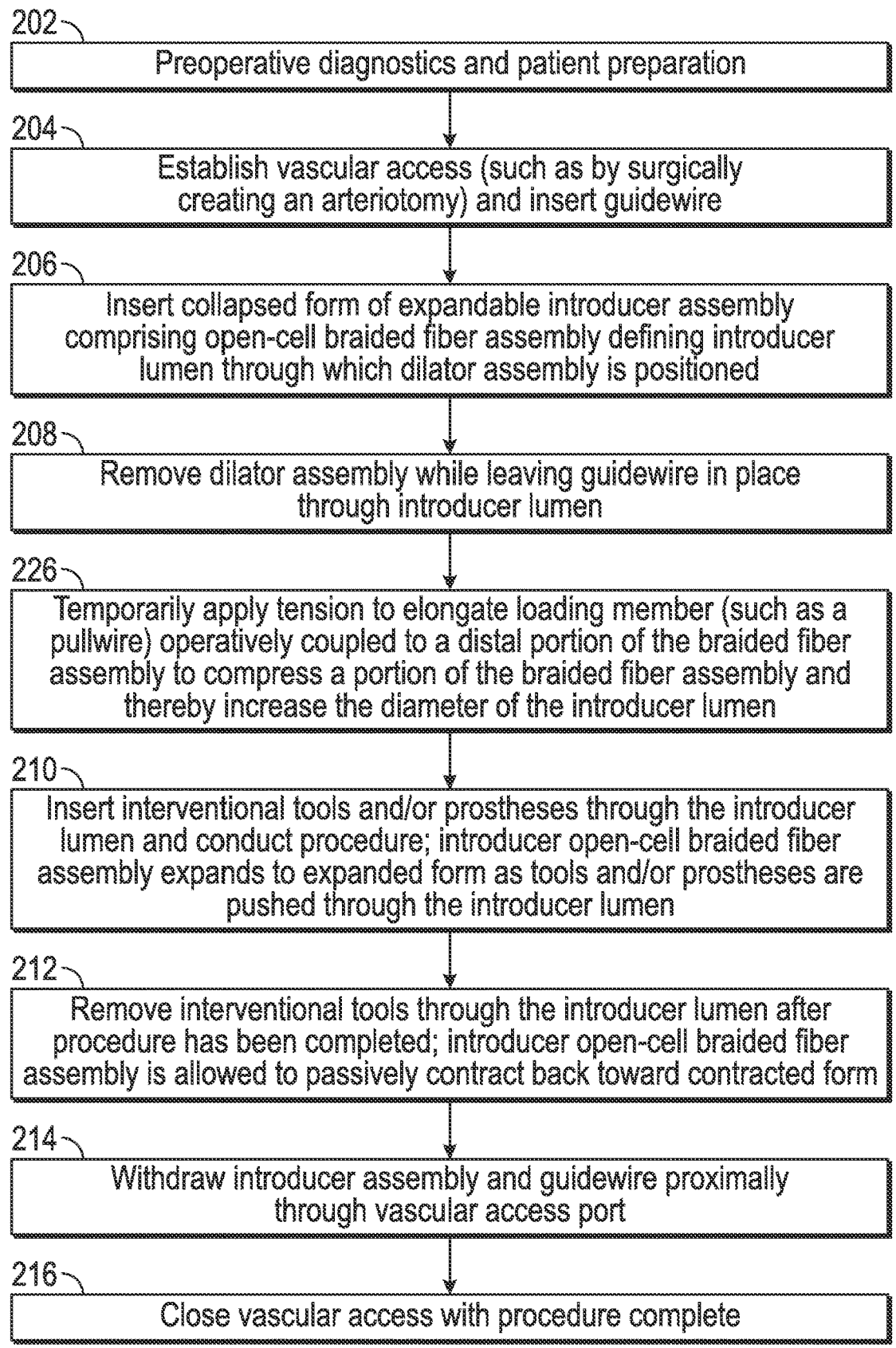
FIG. 5 illustrates various aspects of a minimally invasive surgical access technique in accordance with the present invention.

FIG. 5 illustrates an embodiment similar to that of FIG. 3, with the exception that an additional step is included (226) wherein an elongate loading member may be tensioned to place the braided fibrous expandable sheath into compression, thereby forcibly increasing the diameter of the associated defined introducer lumen for easier passage of structures through such introducer lumen.

Figure 6:
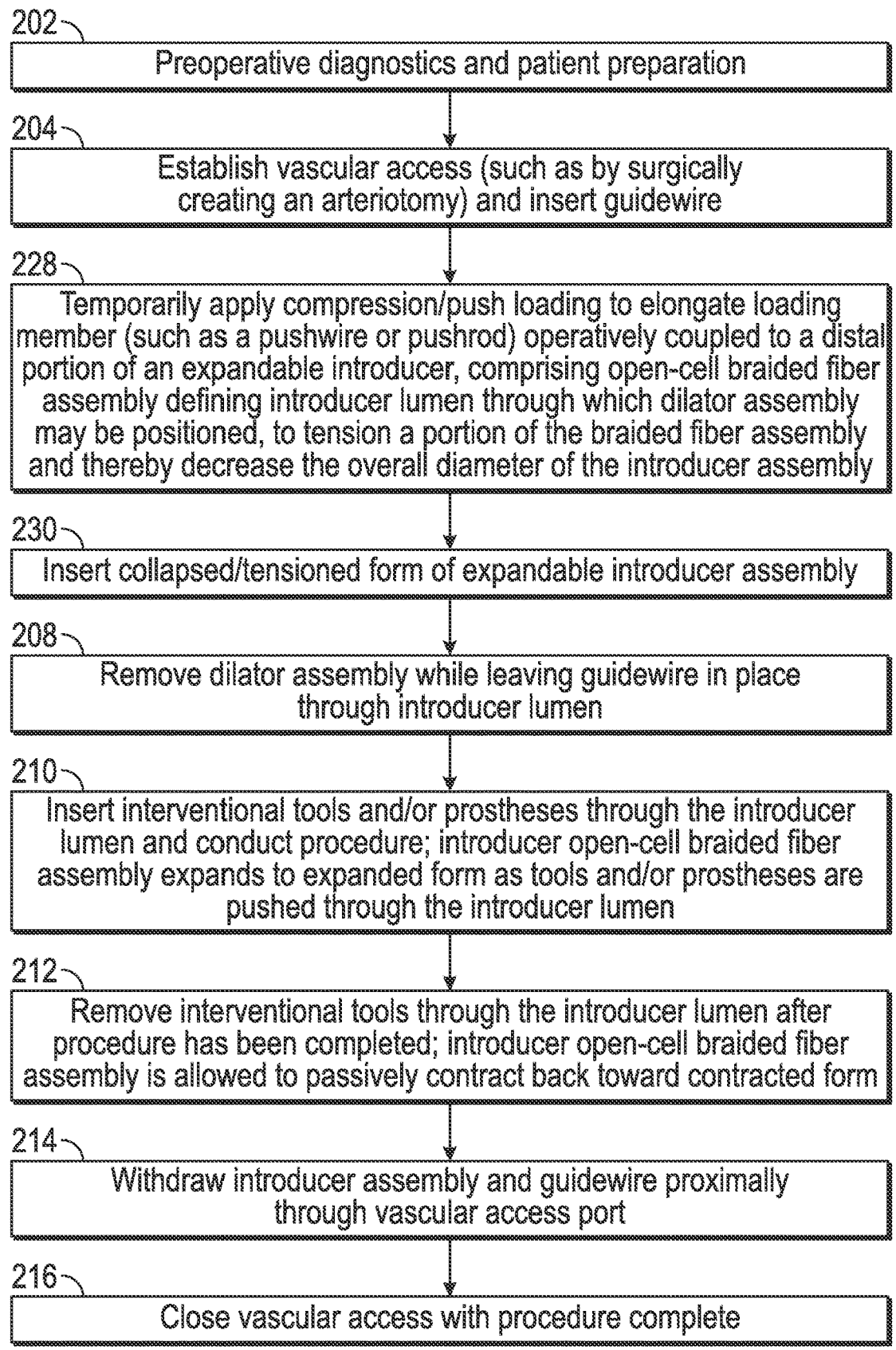
FIG. 6 illustrates various aspects of a minimally invasive surgical access technique in accordance with the present invention.

FIG. 6 illustrates an embodiment similar to that of FIG. 3, with the exception that insertion of the expandable sheath assembly is facilitated by forcibly minimizing the diametric geometry of the expandable sheath using a pushwire to create tensile loading of the expandable sheath during insertion (228, 230).

Figure 7:
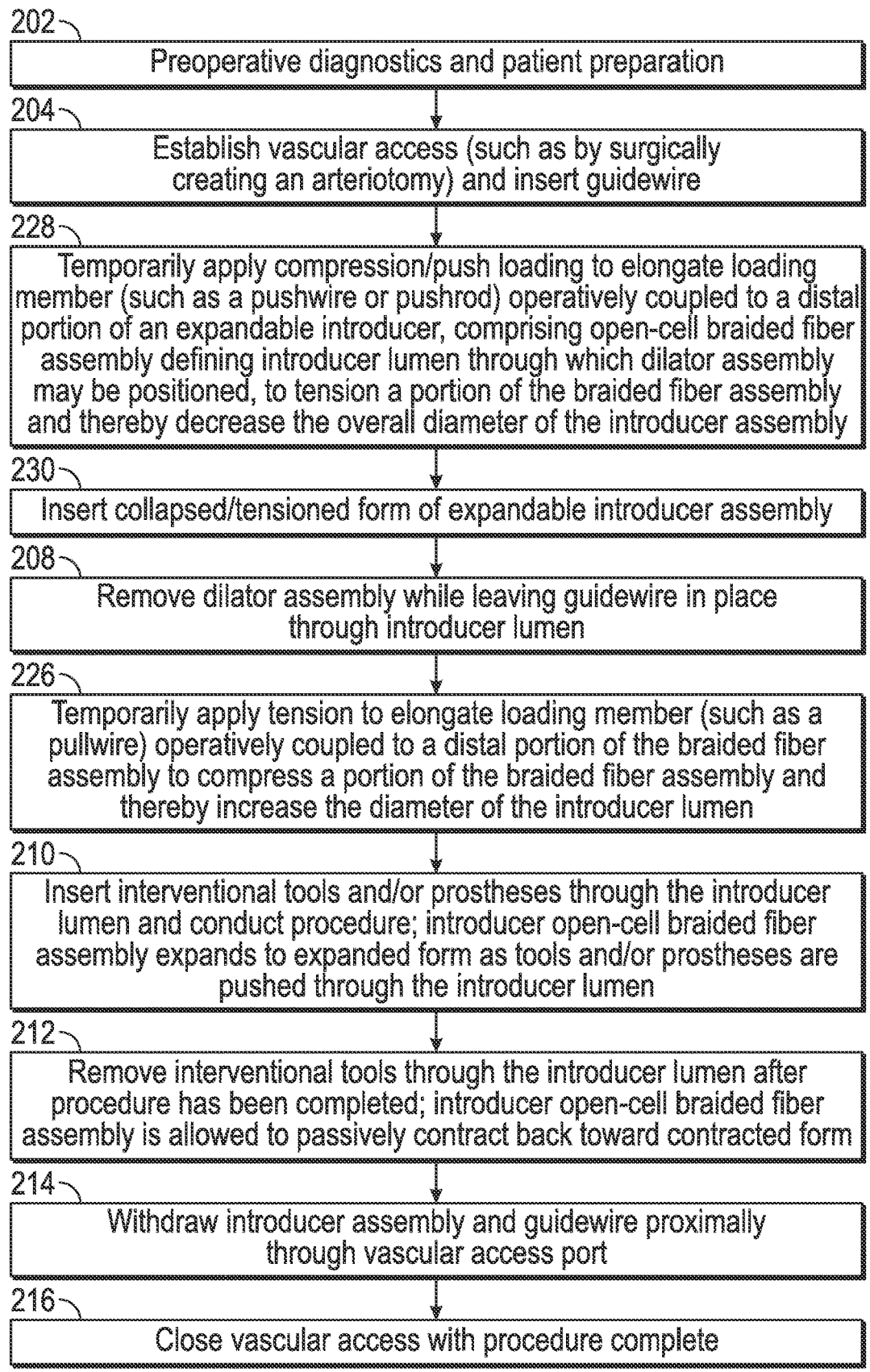
FIG. 7 illustrates various aspects of a minimally invasive surgical access technique in accordance with the present invention.

FIG. 7 combines the differences of the embodiments of FIGS. 5 and 6 relative to that of FIG. 3, both in the same embodiment/procedure, such that tension is controllably applied to minimize the outer geometry of the expandable sheath member during insertion (228, 230), and such that compression is controllably applied to maximize the geometry of the expandable sheath member for insertion of instrumentation therethrough (226).

Figure 8:
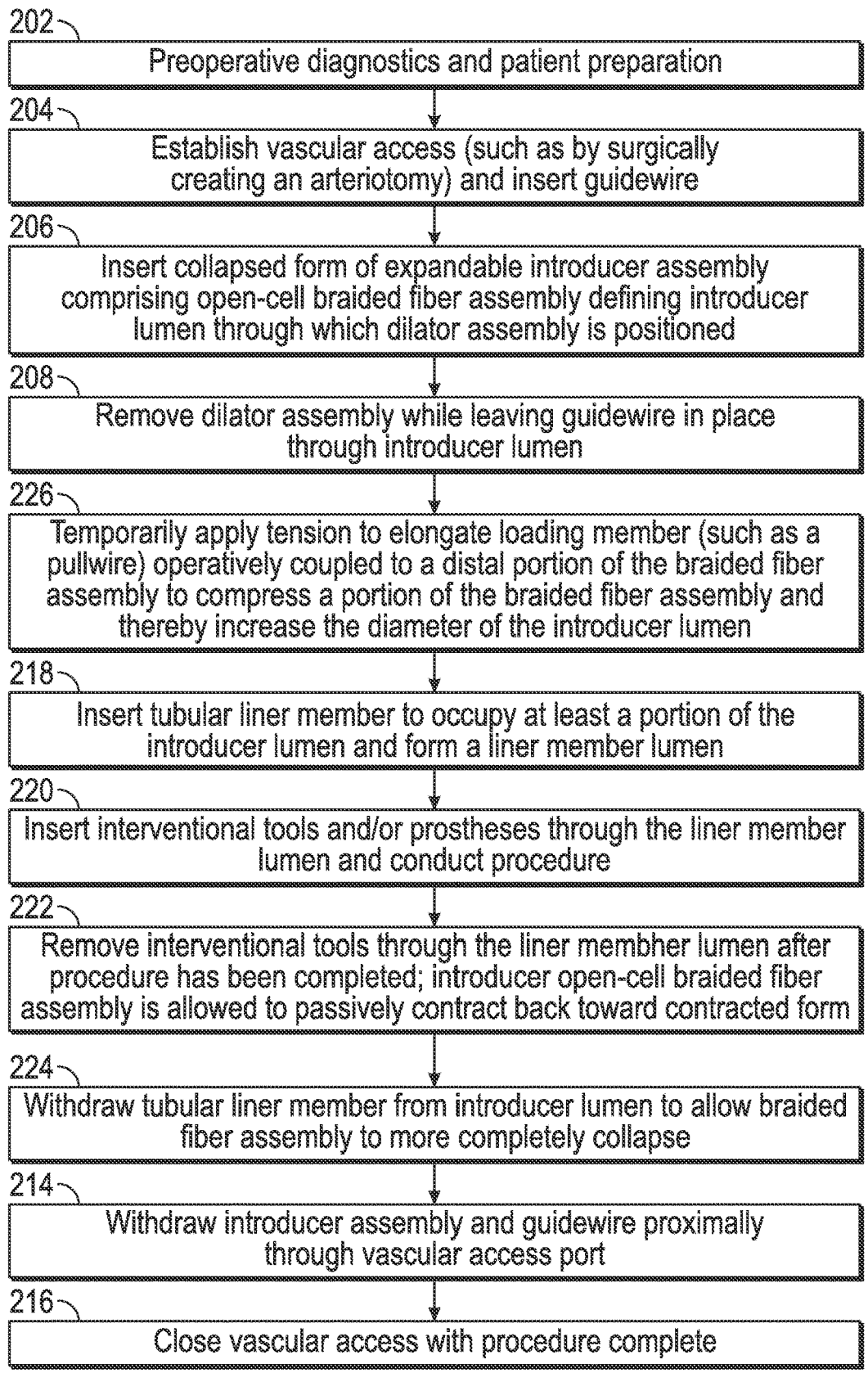
FIG. 8 illustrates various aspects of a minimally invasive surgical access technique in accordance with the present invention.

FIG. 8 illustrates an embodiment similar to that of FIG. 4 wherein a tubular member or liner may be inserted into the expandable sheath to assist with sheath expansion and insertability/retractability of instrumentation (218, 220, 222, 224); also combined into this embodiment is the aforementioned aspect of creating compressive loading of the expandable sheath member to maximize the geometry of the expandable sheath member for insertion of instrumentation therethrough (226).

Figure 9:
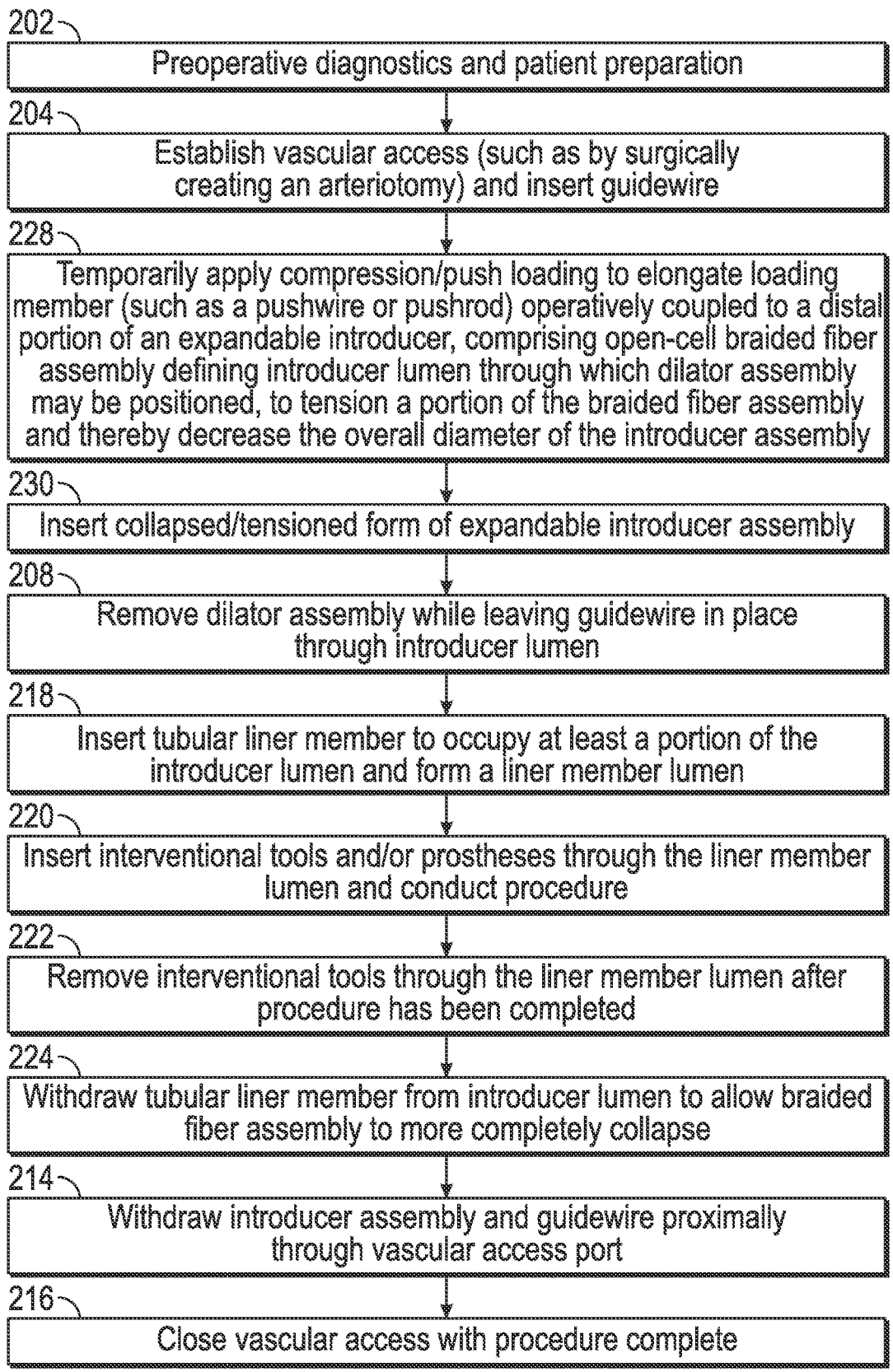
FIG. 9 illustrates various aspects of a minimally invasive surgical access technique in accordance with the present invention.

FIG. 9 illustrates an embodiment similar to that of FIG. 4 wherein a tubular member or liner may be inserted into the expandable sheath to assist with sheath expansion and insertability/retractability of instrumentation (218, 220, 222, 224); also combined into this embodiment is the aforementioned aspect of creating tensile loading of the expandable sheath member to minimize the geometry of the expandable sheath member for insertion or withdrawal from the vasculature (228, 230).

Figure 10:
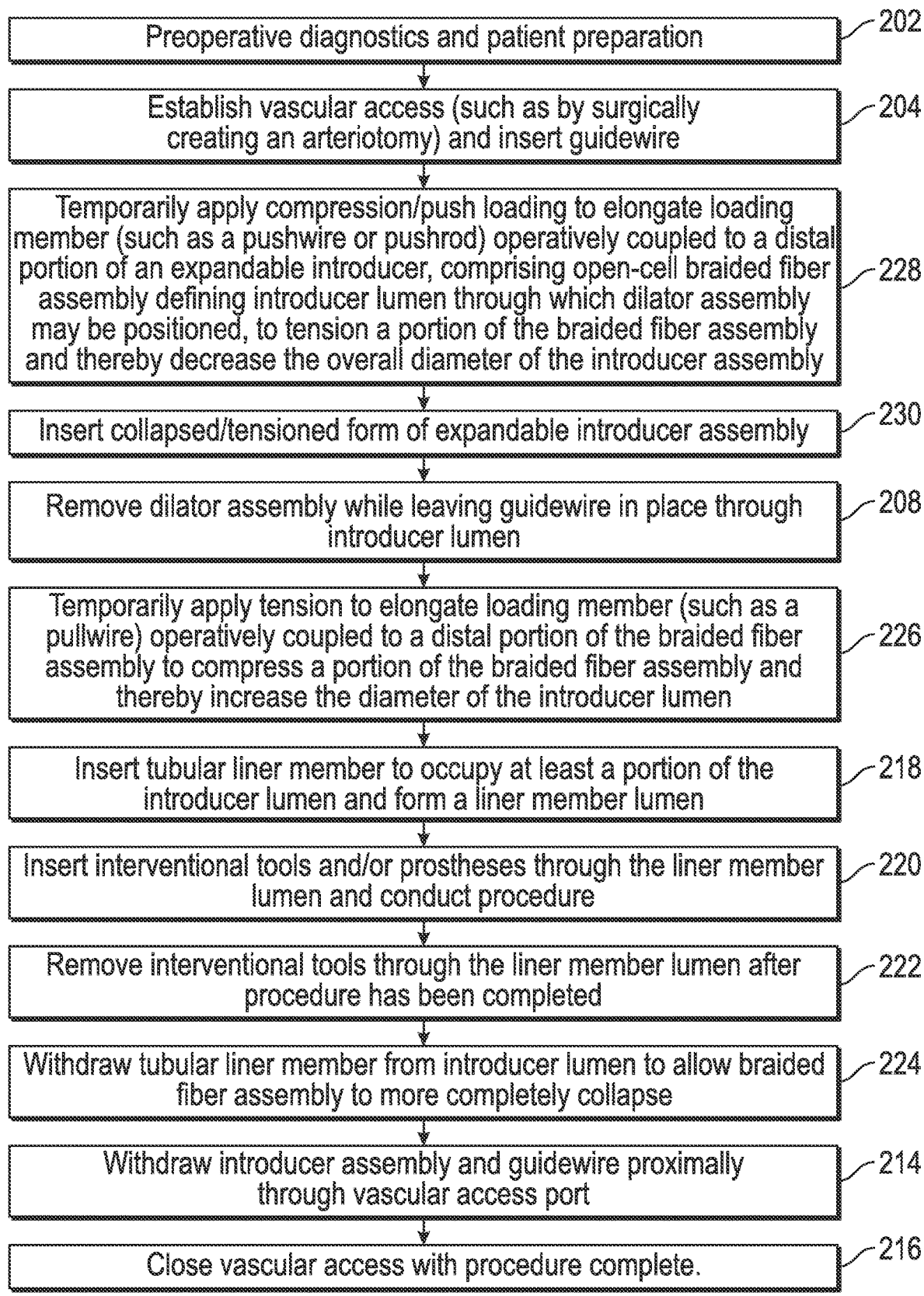
FIG. 10 illustrates various aspects of a minimally invasive surgical access technique in accordance with the present invention.

FIG. 10 illustrates an embodiment similar to that of FIG. 4 wherein a tubular member or liner may be inserted into the expandable sheath to assist with sheath expansion and insertability/retractability of instrumentation (218, 220, 222, 224); also combined into this embodiment is the aforementioned aspect of creating compressive loading of the expandable sheath member to maximize the geometry of the expandable sheath member for insertion of instrumentation therethrough (226), as well as the aforementioned aspect of creating tensile loading of the expandable sheath member to minimize the geometry of the expandable sheath member for insertion or withdrawal from the vasculature (228, 230).

Figure 11:
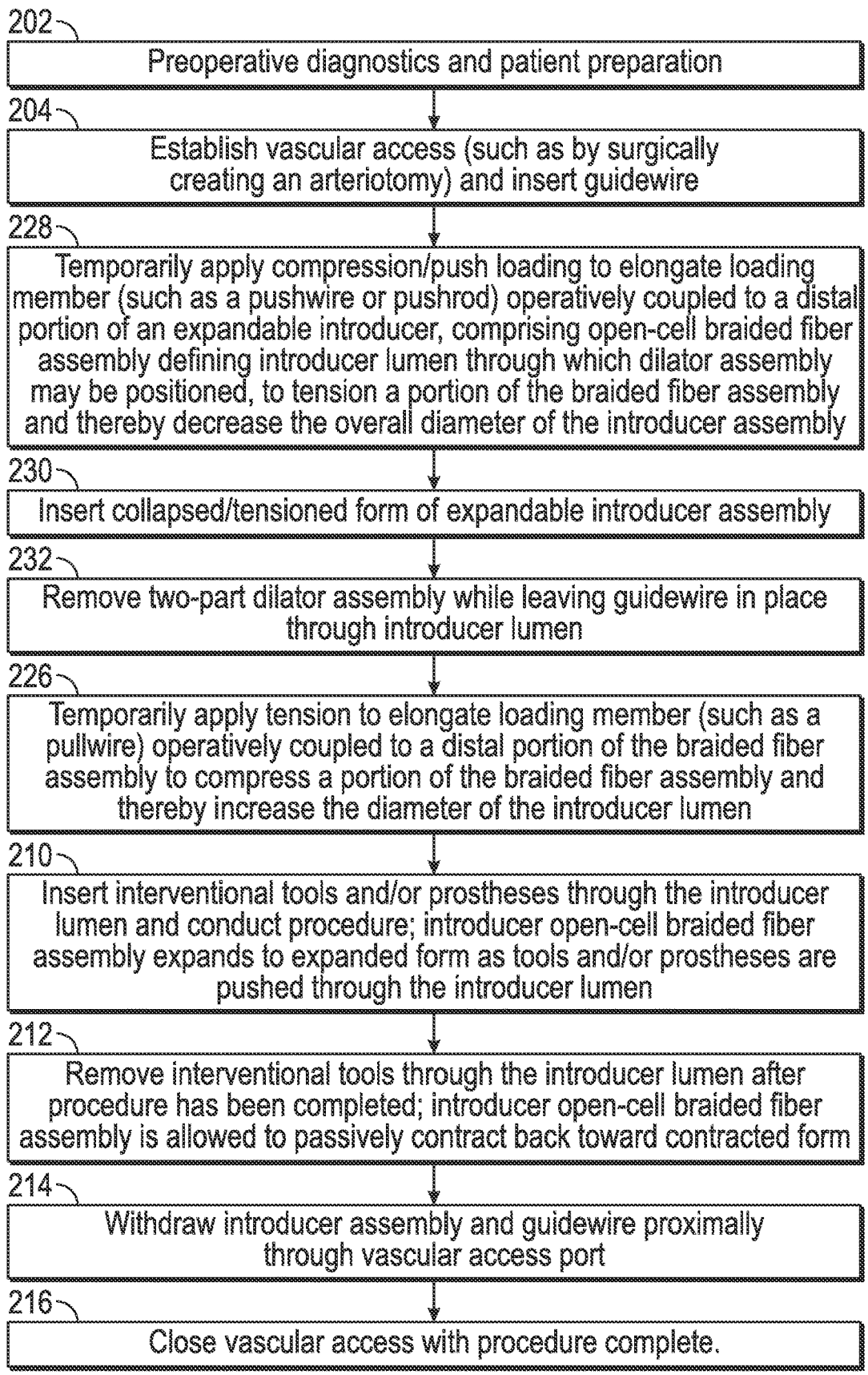
FIG. 11 illustrates various aspects of a minimally invasive surgical access technique in accordance with the present invention.

FIG. 11 illustrates an embodiment similar to that of FIG. 7, with additional emphasis on having a dilator assembly comprising two or more parts (232), such as that shown in FIG. 2J.

Figure 12:
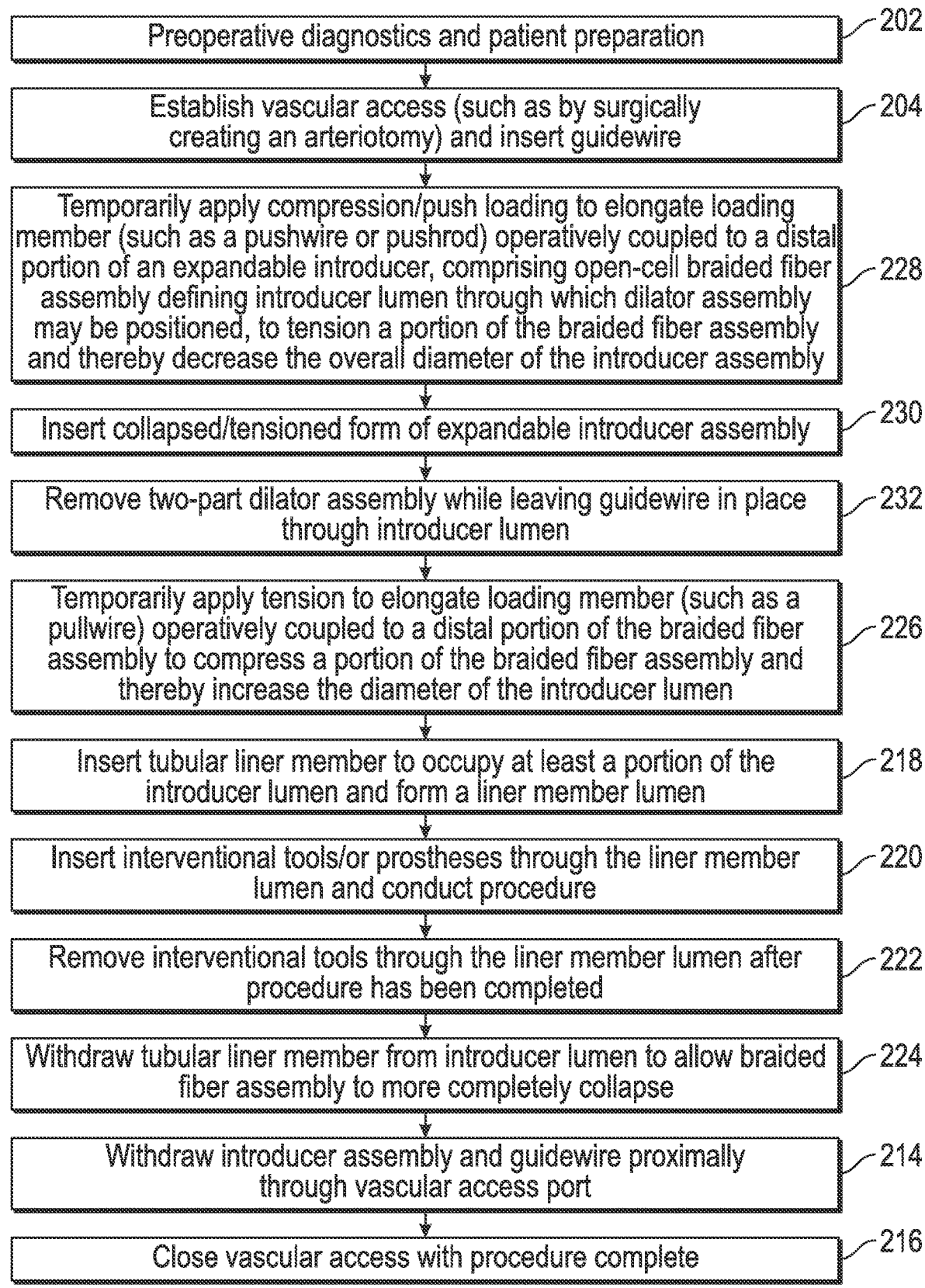
FIG. 12 illustrates various aspects of a minimally invasive surgical access technique in accordance with the present invention.

Similarly, FIG. 12 illustrates an embodiment similar to that of FIG. 10, with additional emphasis on having a dilator assembly comprising two or more parts (232), such as that shown in FIG. 2J.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject diagnostic or interventional procedures may be provided in packaged combination for use in executing such interventions. These supply "kits" may further include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

The invention claimed is:

1. A system for deploying a device to a distal location in a blood vessel comprising:
   a. an elongate introducer sheath comprising a matrix of a plurality of braided fibers to form an open cell fibrous wall having an outer diameter and an inner diameter which defines a lumen therethrough, said sheath being configured to have a first collapsed configuration and to be capable of locally and temporarily transitioning to a second expanded configuration passively and without active manipulation during the passage through the lumen of a device having a diameter larger than said inner diameter of said lumen, at the location occupied by the device during said passage, said sheath comprising a tapered distal portion,
   b. said sheath being sufficiently flexible in the first collapsed configuration to be moved distally through at least a portion of a blood vessel to reach a desired distal location,
   c. said matrix of fibers being capable of locally recollapsing from the second expanded configuration without active manipulation after the device passes to an adjacent portion of the lumen such that said recollapsing is proximal to the device and such that the second expanded configuration of the sheath has a changing location corresponding to the location of the device as the device passes through the sheath, and
   d. a two-part dilator assembly comprising a first dilator member comprising a tapered exterior distal portion, said tapered exterior distal portion coupled to a second dilator member having a distal tip portion and a proximal portion comprising a cavity having a tapered interior surface, said first dilator member located proximally to said second dilator member with said tapered exterior distal portion sized to fit within said cavity and capable of capturing the tapered distal portion of said introducer sheath between said tapered exterior distal portion of the first dilator member and the tapered interior surface of the proximal portion of the second dilator member, the tapered distal portion of the introducer sheath being pulled by the two-part dilator assembly to place the introducer sheath into tension to minimize the outer diameter of the entire introducer sheath during insertion into the blood vessel, wherein upon the tapered distal portion of the introducer sheath being released from the two-part dilator assembly, the entire introducer sheath expands to the first collapsed configuration, wherein said minimized outer diameter of said entire introducer sheath during insertion is less than an outer diameter of said entire introducer sheath in the first collapsed configuration, and wherein said outer diameter of said entire introducer sheath in the first collapsed configuration is less than an outer diameter of said introducer sheath in the second expanded configuration.

2. The system of claim 1 comprising a substantially non-porous expandable layer coupled to a proximal portion of said matrix of fibers and capable of preventing fluids present in the lumen from crossing the matrix of fibers.

3. The system of claim 1 wherein said system is capable of deploying an implantable cardiac valve prosthesis.

4. The system of claim 1 wherein said matrix of fibers comprise a polymeric material.

5. A system for deploying a device to a distal location in a blood vessel comprising:
   a. an elongate introducer sheath comprising a matrix of a plurality of braided fibers to form an open cell fibrous wall having an outer diameter and an inner diameter which defines a lumen therethrough, said sheath being configured to have a first collapsed configuration capable of transitioning to a second expanded configuration, said sheath being suitable for use for deploying a device having a diameter larger than a diameter of a proximal part of said sheath, said sheath comprising a tapered distal portion,
   b. said sheath being sufficiently flexible in the first collapsed configuration to be moved distally through at least a portion of a blood vessel to reach a desired distal location,
   c. a two-part dilator assembly comprising a first dilator member having a tapered exterior distal portion coupled to a second dilator member having a distal tip portion and a proximal portion comprising a cavity having a tapered interior surface, said first dilator member located proximally to said second dilator member with said tapered exterior distal portion sized to fit within said cavity and capable of capturing the tapered distal portion of said introducer sheath between the tapered exterior distal portion of the first dilator member and the tapered interior surface of the proximal portion of the second dilator member, the tapered distal portion of the introducer sheath being pulled by the two-part dilator assembly to place the introducer sheath into tension to minimize the outer diameter of the entire introducer sheath during insertion into the blood vessel;
   d. a hub, said introducer sheath being coupled to the hub; and
   e. a locking member temporarily positioned between the hub and the proximal portion of the second dilator member to maintain the tension on the introducer sheath,
   wherein said minimized outer diameter of said entire introducer sheath during insertion is less than an outer diameter of said entire introducer sheath in the first collapsed configuration, and wherein said outer diameter of said entire introducer sheath in the first collapsed configuration is less than an outer diameter of said introducer sheath in the second expanded configuration.

6. The system of claim 5 wherein upon removal of the locking member, the introducer sheath expands to the first collapsed configuration.

7. An expandable introducer sheath comprising:
   an expandable and contractible tubular shaft comprising a lumen sized and expandable to receive a positionable medical device therethrough, wherein the expandable and contractible tubular shaft includes a plurality of braided fibers arranged in a mesh pattern;
   a sealing layer apart from the expandable and contractible tubular shaft, wherein the sealing layer is positioned along the expandable and contractible tubular shaft, and further wherein a porosity of the sealing layer is less than a porosity of the expandable and contractible tubular shaft; and
   a proximal hub operably coupled to a proximal end of the expandable and contractible tubular shaft,
   wherein the entire expandable and contractible tubular shaft is pulled into tension to have an outer diameter during insertion into a blood vessel less than an outer diameter of the entire expandable and contractible tubular shaft in a first collapsed configuration, and
   wherein the outer diameter of the entire expandable and contractible tubular shaft in the first collapsed configuration is less than an outer diameter of the expandable and contractible tubular shaft in a second expanded configuration.

* * * * *